United States Patent [19]

Conn et al.

[11] Patent Number: 4,704,472

[45] Date of Patent: Nov. 3, 1987

[54] PREPARATION OF AN ENANTIOMER OF A SUBSTITUTED FLUORENYLOXYACETIC ACID

[75] Inventors: Robin S. E. Conn, Westfield; Sandor Karady, Mountainside, both of N.J.

[73] Assignee: Merck & Co., Inc., Rahway, N.J.

[21] Appl. No.: 797,311

[22] Filed: Dec. 18, 1985

[51] Int. Cl.$^4$ .................. C07C 59/76; C07C 65/34
[52] U.S. Cl. ........................... 562/461; 560/053; 560/056; 562/466; 568/327
[58] Field of Search .............. 562/461, 466; 560/053, 560/056

[56] References Cited

U.S. PATENT DOCUMENTS 4,316,043 2/1982 Cragoe et al. .................. 562/461

Primary Examiner—Paul J. Killos
Attorney, Agent, or Firm—Charles M. Caruso; Hesna J. Pfeiffer

[57] ABSTRACT

A process for direct preparation of an enantiomer of a substituted fluorenyloxyacetic acid is disclosed. The acetic acid derivative is useful for treating brain edema.

8 Claims, No Drawings

PREPARATION OF AN ENANTIOMER OF A SUBSTITUTED FLUORENYLOXYACETIC ACID

BACKGROUND OF THE INVENTION

The invention is principally concerned with a process for direct preparation of enantiomers of a substituted fluorenyloxyacetic acid.

Certain fluorenyloxyacetic acids useful for treating brain edema are disclosed in U.S. Pat. No. 4,316,043. These acetic acids have a chiral center and exist as racemates and individual isomers. A chiral catalytic process for producing such compounds is described in U.S. Pat. No. 4,587,357 of Bhattacharya filed Oct. 1, 1984.

A process has been discovered for directly preparing individual isomers of a fluorenyloxyacetic acid which is simpler and requires less catalyst than the Bhattacharya application hereinabove.

SUMMARY OF THE INVENTION

A process for preparing an isomer of a substituted fluorenyloxyacetic acid.

DETAILED DESCRIPTION OF THE INVENTION

An embodiment of the present invention is a process for preparing an enantiomer compound of the formula:

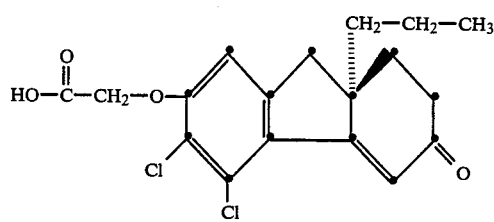

from compound II wherein R is alkyl, benzyl, or oxyacetic acid loweralkyl ester, which comprises:

(a) treating a compound of the formula:

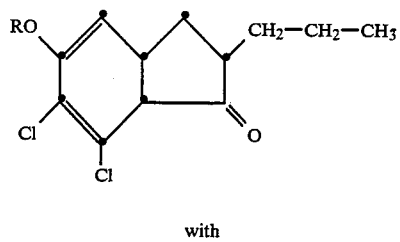

with

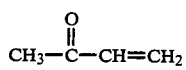

where R is alkyl or benzyl in a basic medium in the presence of a chiral catalyst to obtain:

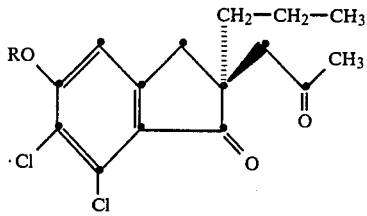

wherein R is $C_1$-$C_6$ alkyl, or benzyl (b) cyclizing IV to obtain

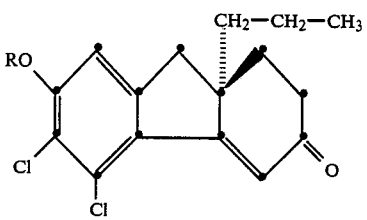

(c) dealkylation to obtain

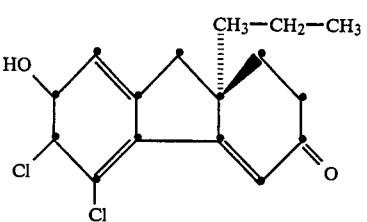

(d) alkylating VI to obtain

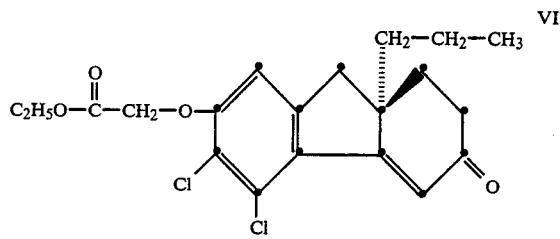

(e) treating VII with base and neutralizing to obtain an enriched mixture containing a compound of the structure

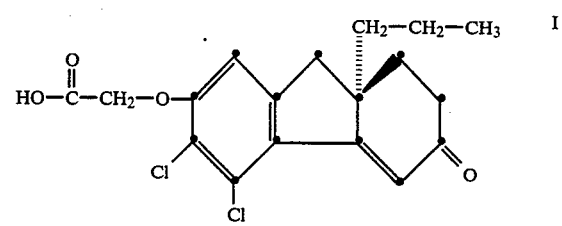

or where R is oxyacetic acid loweralkyl ester by
(a') treating compound II with

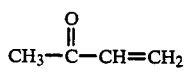

in the presence of a chiral catalyst in a basic medium, to obtain compound IV, (e') treating compound IV with an excess of a strong base followed by neutralization to obtain directly an enriched mixture containing I, (f) and isolating the enantiomer I by known resolution means to obtain the I enantiomer.

The compound I is useful for treating brain edema as described in U.S. Pat. No. 4,316,043.

Any suitable chiral catalyst may be used and dihydro-N-benzylcinchonidinium or N-benzylcinchonidinium halide wherein benzyl is substituted or unsubstituted or wherein substituents (1 or 2) are selected from $CF_3$, halo, $C_1$–$C_3$, alkyl, $OCH_3$, CN, and the like including 3,4-dichlorobenzyl cinchonidinium chloride and p-trifluoromethyl cinchonidinium bromide is preferred. Dihydro-3,4-dichlorobenzyl cinchonidinium chloride and (ii) dihydro-p-trifluoromethyl benzyl cinchonidinium bromide are particularly preferred. Using these chiral catalysts, formula IV compound containing the (R) isomer predominantly is obtained; the ratio of (R); (S) isomer will range from 60:40 to 76:24 or higher.

Step (a) involves Michael addition of a ketone III to the racemic formula II substituted indanone in a basic medium in th presence of a chiral catalyst. The basic medium is generally a strong base, e.g. KOH, NaOH, etc. The base may be solid KOH or NaOH as an aqueous solution of the base. A nonaqueous solvent is also required. This solvent may be any suitable hydrocarbon such as benzene, toluene, or mixtures with alkanes and the like. It is also possible to make a solution of the catalytic species in toluene by partitioning the catalyst between toluene and aqueous NaOH. Then the aqueous NaOH may be removed and the reaction can be carried out in the toluene solution of catalyst. The step (a) reaction is conveniently carried out at atmospheric pressure and at temperatures ranging from about 0° C. to about 30° C., and preferably at room temperature (25° C.). The amount of catalyst which is used can be varied and may range from about 2 to about 100 mole percent. This step is also characterized by requiring 1 mole of the ketone III per mole of formula II.

The formula IV product from step (a) is obtained rich in the (R) isomer. This isomer rich formula IV product is then cyclized by treatment eg with $H_2SO_4$, dealkylated by treatment with an aluminum halide, e.g. aluminum chloride in a suitable solvent, alkylated in step (d) to obtain VII which is treated with a strong base such as NaOH, KOH, LiOH, $Na_2CO_3$ and the like and neutralized to produce material enriched in the (R) isomer of formula I, the free acid. The free acid, rich in (R) isomer, is then further resolved by known methods to obtain the pure R isomer I.

The following example illustrates the process of the present invention. All temperatures are in 0° C. unless otherwise indicated.

EXAMPLE 1

(A)
6,7-Dichloro-2,3-dihydro-5-methoxy-2-(3-oxobutyl)-2-propyl-1H-inden-1-one

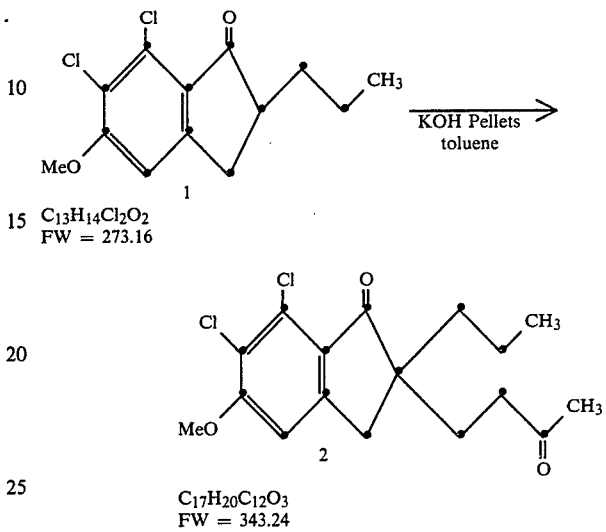

Materials 6,7-dichloro-2,3-dihydro-5-methoxy-2-propyl-1H-inden-1-one (1): 100 g (0.366 mol)
Methyl vinyl ketone: 26.17 g (31.09 ml, 0.366 mol; 98% purity)
Dihydro-3,4-dichlorobenzylcinchonidinium chloride: 10 g (0.020 mol, 5.6 mol%)
Potassium hydroxide pellets; 40 g
Toluene: 2.8 l
1N hydrochloric acid A 5 liter 3-necked flask was equipped with a mechanical stirrer, a 250 ml pressure equalizing addition funnel and an $N_2$ inlet going to a manifold or a Firestone valve. The indanone 1 (100 g) was charged and dissolved in 2.5 l of toluene. This solution was degassed by alternately applying vacuum and nitrogen and left under a nitrogen atmosphere.

The chiral catalyst (10 g) and potassium hydroxide (40 g) were charged under a positive pressure of nitrogen. The methyl vinyl ketone was dissolved in 100 ml of toluene and added by addition funnel over 5–10 minutes.

The reaction was stirred at 25° and monitored by LC. It was completed in 1.5 hr.

Upon completion of the reaction, the solid potassium hydroxide was filtered and washed with 200 ml of toluene. The combined organics were washed with 1 l of 1N HCl.

The toluene solution of indanone 2 may be dried by azeotropic distillation. It assays at 92 wt % yield, 96 area % purity and 40% e.e. [70:30 enantiomer ratio of (R) to (S) isomers].

This experiment is repeated using dihydro p-trifluoromethylbenzylcinchonidinium chloride and the catalyst in the following manner:

6,7-dichloro-2,3-dihydro-5-methoxy-2-propyl-1H-indene-1-one (1): 2.73 g, 0.01 mol
Methyl vinyl ketone: 0.72 g (0.85 ml, 0.01 mol; 98% purity)

Dihydro-p-trifluoromethylbenzylcinchonidinium chloride: 0.5 g
Sodium hydroxide, 50% aqueous: 15 ml
Toluene 100 ml
1N hydrochloric acid: 50 ml A 250 ml, 3-necked flask was equipped with mechanical stirring, a pressure equalizing addition funnel and nitrogen flushed. The indanone 1 (2.73 g) was charged and dissolved in 70 ml of toluene. The catalyst (0.5 g) was added followed by 15 ml of 50% aqueous NaOH. The mixture was stirred at 25° and the methyl vinyl ketone (0.72 g) dissolved in 30 ml of toluene was added dropwise over 0.5 hour. The reaction was stirred for 5 minutes after the completion of the addition. The reaction was shown to be complete by LC. The layers were separated and the organic layer was washed with 1N HCl (50 ml). The e.e. was 52%, favoring the R isomer.

(B) Cyclization 5,6-Dichloro-1,2,9,9a-tetrahydro-7-methoxy-9a-propyl-3H-fluoren-3-one (3)

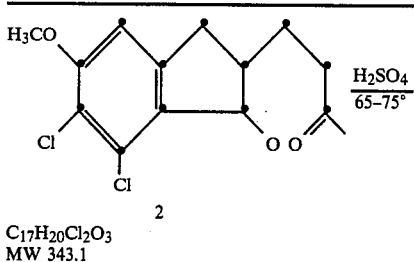

2
$C_{17}H_{20}Cl_2O_3$
MW 343.1

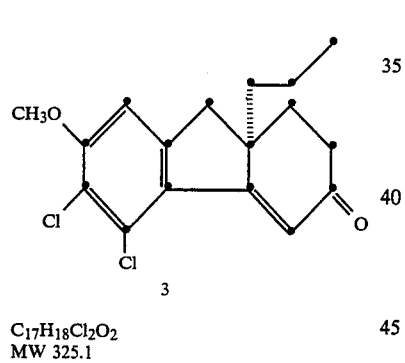

3
$C_{17}H_{18}Cl_2O_2$
MW 325.1

| | | Materials |
|---|---|---|
| 17.9 g | 55.3 mmole | 6,7-Dichloro-2,3-dihydro-5-methoxy-2-propyl-2-(3-oxobutyl)-1H—inden-1-one (2) (783 ml of a toluene solution, containing 25.55 mg/ml of 2 (76/24 enantiomer ratio) |

An aliquot of the toluene solution containing 17.9 g (55.3 mmoles) is concentrated in vacuo and 50 ml concentrated sulfuric added to the concentrated at a rate of 10 ml/minute with cooling to maintain a temperature of 0°–5° during the addition. The cooling is removed and 2 ml of water is added. The reaction mixture is then heated to 60°–65° C. for a period of 30 minutes.

The reaction mixture is cooled to 25° C. and then slowly poured over 20 minutes into a stirred mixture of 150 ml of toluene and 275 ml of water allowing the temperature to rise to 35°. The residue in the flask is transferred successively with 5 ml concentrated $H_2SO_4$, and 2 times 10 ml of a 1:1 mixture of toluene and water. The heterogenous mixture is stirred for 15 minutes at 50° and then allowed to separate at 50°. The aqueous layer is discarded. To the toluene layer containing the product is added 200 ml of a 5% sodium bicarbonate solution and the heterogeneous mixture is stirred for 60 minutes at 20°–25° and then allowed to separate. The aqueous layer is discarded. To the toluene layer containing the product is added 60 ml 1N HCl. The heterogeneous mixture is stirred for 30 minutes at 20°–25° and then allowed to settle. The bottom aqueous layer is separated from the top toluene layer. The aqueous layer is discarded. The toluene layer containing the product is carried through to the next step.

(C) O-Demethylation 5,6-Dichloro-1,2,9,9a-tetrahydro-7-hydroxy-9a-propyl-3H-fluoren-3-one

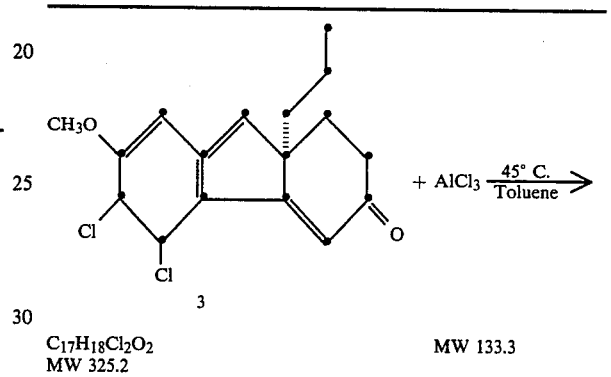

3
$C_{17}H_{18}Cl_2O_2$
MW 325.2

MW 133.3

4
$C_{16}H_{16}Cl_2O_2$
MW 311.2

| | | Materials |
|---|---|---|
| 15.43 g | 47.4 mmole | Approximately 200 ml solution of 5,6-dichloro-1,2,9,9a-tetrahydro-7-methoxy-9a-propyl-3H—fluoren-3-one 3 in toluene. |
| 22.1 g | 166 mmole | Aluminum chloride (3.5 moles per mole of 6) |
| 34 ml | | Water |
| 30 ml | | Toluene |

The volume of the reaction mixture is adjusted to 230 ml with 30 ml of toluene. The toluene solution is dried by azeotropic removal of water at reflux to a KF of 0.1%. The solution is cooled to room temperature (20° C.) and the aluminum chloride is added over a period of 5 minutes. The temperature rises to 37° C. The mixture is heated to 45°–48° C. and aged at that temperature for 1.5 hours.

Completion of the demethylation is monitored by LC.

The reaction is quenched at 45°–47° C. by addition of 34 ml of water. The temperature rises to 75° C. The grey reaction mixture is then heated to reflux and aged at reflux for 1 hour. The reaction mixture is then dried by azeotropic removal of water.

(D) O-Alkylation

[(5,6-Dichloro-2,3,9,9a-tetrahydro-3-oxo-9a-propyl-1H-fluoren-7-yl)oxy]acetic Acid Ethyl Ester

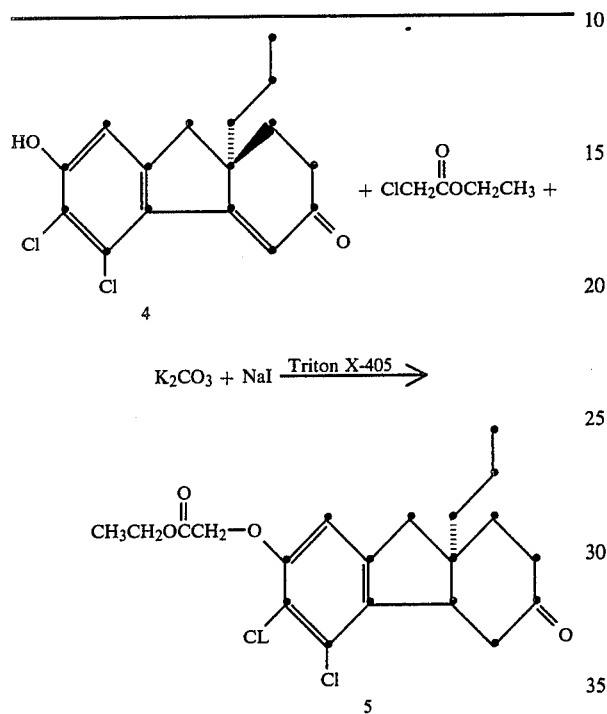

| Approx. 14.7 g | 47.4 mmole | 5,6-Dichloro-1,2,9,9a-tetrahydro-7-hydroxy-9a-propyl-3H—fluoren-3-one in approx. 230 ml of toluene. |
|---|---|---|
| 3.9 g | | Triton X-405, 25 wt. % based on Indanone 3. |
| 29.5 g | 213 mmole | Potassium carbonate (1 mole per mole of aluminum chloride and 3 used in the previous step). |
| 2.3 g | 15.3 mmole | Sodium iodide |
| 9.57 g | 78.1 mmole | Ethyl chloroacetate |
| 250 ml | | 2.5 N Hydrochloric acid |
| 250 ml | | 1.0 N Hydrochloric acid |

To the reaction mixture from the previous step is added 3.9 g of Triton X-405, 29.5 g of potassium carbonate, 2.3 g of sodium iodide and 9.57 g of ethyl chloroacetate. The reaction mixture is heated to reflux and water is azeotropically removed. The reaction is aged for 4 hours at reflux while the water is removed. The reaction mixture is cooled to room temperature and 250 ml of 2.5N HCl is slowly added (CO₂ evolution!). The mixture is heated to 70°–75° C. and stirred for 0.5 hours. The bottom aqueous layer is cut at 70°–75° C. and discarded. The toluene layer containing the product is washed with 250 ml of 1N HCl at 75° C. The toluene layer is cooled to room temperature (20° C.). Yield 18.2 g (96.6% from 4).

(E) Ester Hydrolysis

[(5,6-Dichloro-2,3,9,9a-tetrahydro-3-oxo-9a-propyl-1H-fluoren-7-yl)oxy] Acetic Acid Potassium Salt

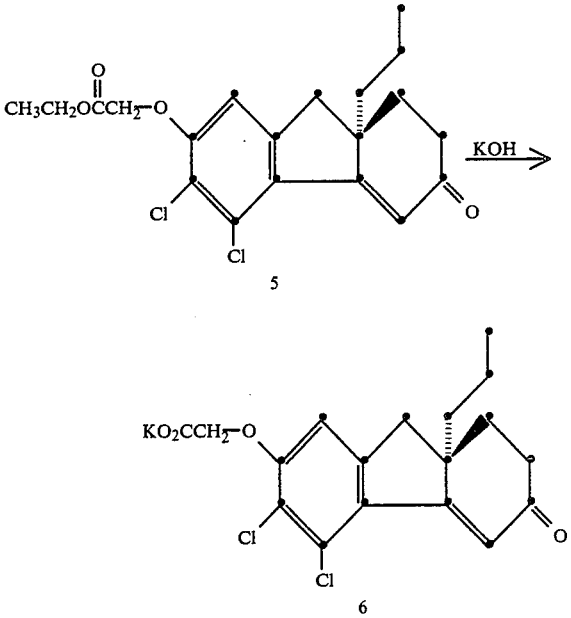

| Approx. 18.2 g | 45.8 mmole | [(5,6-Dichloro-2,3,9,9a-tetrahydro-3-oxo-9a-propyl-1H—fluoren-7-yl)-oxy] acetic acid ethyl ester in approx. 230 ml of toluene from previous step. |
|---|---|---|
| 101 ml | | 1.17 N Potassium hydroxide (2.5 mole KOH/mole of 8) |
| 165 ml | | Water |

Water (165 ml) and 101 ml of 1.17N potassium hydroxide solution (2.5 mole KOH/mole of 5) are added to the toluene solution from the previous step. After mixing, the pH of the aqueous phase is 13.2. The mixture is refluxed for 2 hours and then cooled to 75° C. The bottom aqueous layer containing the product is separated and cooled to 20° C. Yield 15.7 g of 6 (as acid) (89.8% from 3), (R/S) Isomer ratio=76/24.

What is claimed is:

1. A process for preparing an optical isomer of a compound of the formula:

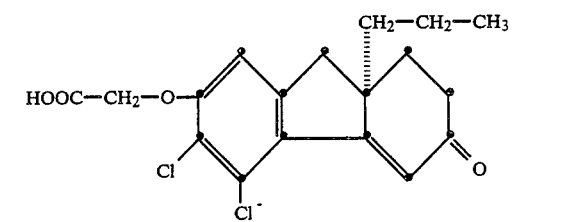

from compound II wherein R is loweralkyl, benzyl or $C_1$-$C_6$alkyl—OOCCH$_2$—O—, which comprises:

(a) treating a compound of the formula:

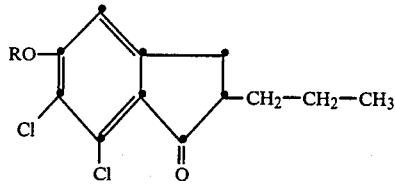

with

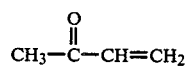

wherein R is loweralkyl or benzyl in a basic medium in the presence of a cinchonidinium chiral catalyst to obtain:

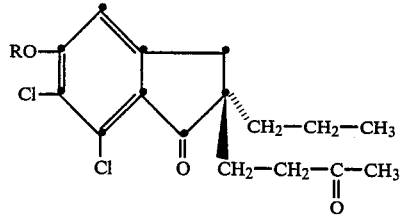

rich in the (R) isomer wherein R is $C_1$–$C_6$ alkyl or benzyl, (b) cyclizing IV to obtain

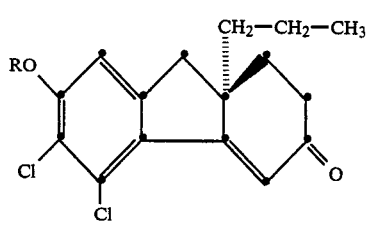

(c) dealkylation to obtain

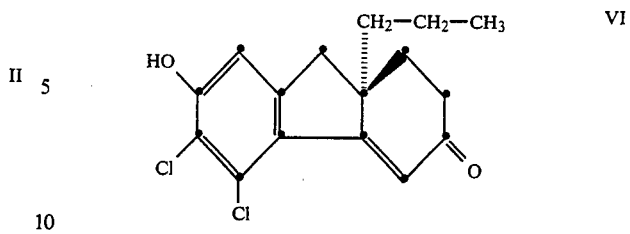

(d) alkylating IV to obtain

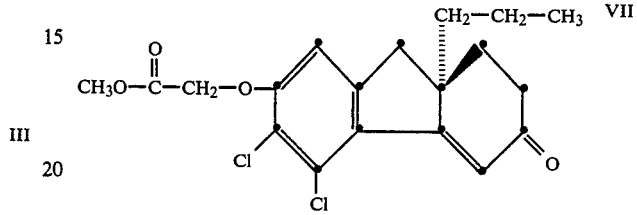

(e) treating VII with base and neutralizing to obtain an enriched mixture containing a compound of the structure

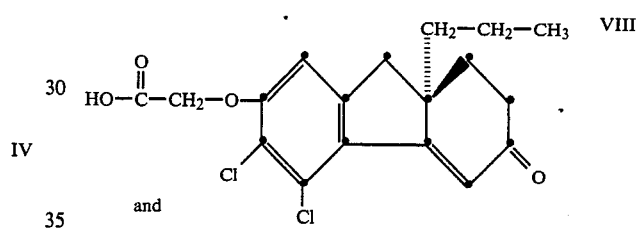

and or wherein R is oxyacetic acid loweralkyl ester
(a') treating compound II with

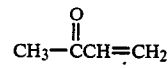

in the presence of a chiral catalyst in a basic medium to obtain compound IV,
(e') treating compound IV with an excess of a strong base followed by neutralization to obtain directly an enriched mixture containing I,
(f) and isolating enantiomer I by known resolution means to obtain the I isomer.

2. The process of claim 1 wherein R is $CH_3$.

3. The process of claim 1 wherein R is oxyacetic acid methyl ester.

4. The process of claim 1 wherein said chiral catalyst is a dihydro benzyl cinchonidinium halide.

5. The process of claim 4 wherein said catalyst is dihydro-3,4-dichlorobenzylcinchonidinium chloride.

6. The step (a) process of the claim 1 process.

7. The process of claim 6 wherein said catalyst is dihydro-3,4-dichlorobenzylcinchonidinium chloride.

8. The process of claim 6 wherein said catalyst is dihydro-p-trifluoromethylcinchonidinium bromide.

* * * * *